United States Patent [19]

O'Neill et al.

[11] Patent Number: 5,446,211

[45] Date of Patent: Aug. 29, 1995

[54] CHLORINATION OF DIFLUOROMETHYL METHYL ETHER

[75] Inventors: Gerald J. O'Neill, Arlington, Mass.; Robert J. Bulka, Merrimack, N.H.

[73] Assignee: Hampshire Chemical Corp., Lexington, Mass.

[21] Appl. No.: 221,498

[22] Filed: Apr. 1, 1994

[51] Int. Cl.$^6$ .................. C07C 41/00; C07C 43/00
[52] U.S. Cl. .................. 568/684; 568/681; 204/157.92
[58] Field of Search .................. 568/684, 681; 204/157.92

[56] References Cited

U.S. PATENT DOCUMENTS

| | | | |
|---|---|---|---|
| 2,066,905 | 1/1937 | Booth | 260/151 |
| 2,533,132 | 12/1950 | McBee | 260/653 |
| 3,461,213 | 8/1969 | Terrell | 568/684 |
| 3,663,715 | 5/1972 | Terrell | 568/684 |
| 3,689,459 | 9/1972 | Reagan | 260/614 F |
| 3,806,602 | 4/1974 | Croix | 424/342 |
| 3,862,241 | 1/1975 | Terrell | 568/684 |
| 3,879,474 | 4/1975 | Croix | 260/614 F |
| 3,887,439 | 6/1975 | Hutchinson | 203/63 |
| 3,897,502 | 7/1975 | Russell et al. | 260/614 F |
| 4,025,567 | 5/1977 | Hutchinson | 260/616 |
| 4,113,435 | 9/1978 | Lagow et al. | 422/191 |
| 4,149,018 | 4/1979 | Bell et al. | 568/684 |
| 4,874,901 | 10/1989 | Halpern et al. | 568/683 |
| 4,961,321 | 10/1990 | O'Neill et al. | 62/114 |
| 5,185,474 | 2/1993 | O'Neill | 568/684 |
| 5,196,600 | 3/1993 | O'Neill | 568/684 |
| 5,278,342 | 1/1994 | O'Neill et al. | 568/684 |

FOREIGN PATENT DOCUMENTS 949978 6/1974 Canada .................. 568/684

OTHER PUBLICATIONS

Chemical Abstract, vol. 52, 44676 (1958).
Journal of the American Chemical Society, 79, 5493–6 (1957).
Chemical Abstract, vol. 55, 27013 (1961).
Chemical Abstract, vol. 55, 12270 (1961).
Chemical Abstract, vol. 55, 23312 (b) (1961).
Chemical Abstract, vol. 55, 27012 (i) (1961).
Chemical Abstract: vol. 56, 9938 (c) (1962).
Chemical Abstract; vol. 58, 2356 (g) (1964).
Chemical Abstract; vol. 73, 14080 (v) (1970).
Chemical Abstract, vol. 82, 43287 (j) (1975).
Parks et al., "J. Amer. Chem. Soc." vol. 76 (1954) pp. 1387–1388.
Parks et al. "J. Amer. Chem. Soc." vol. 74 (1952) pp. 2292–2293.
Soborovskii, Zhur, Obschei, Khina; 29 p. 11134 (1959).

*Primary Examiner*—Johann Richter
*Attorney, Agent, or Firm*—Nields & Lemack

[57] ABSTRACT

The synthesis of fluorinated dimethyl ethers of the formula $CF_2HOCCl_xF_yH_{3-(x+y)}$ wherein x is 0, 1 or 2; y is 1, 2 or 3; and wherein (x+y) is 1, 2 or 3. The process involves chlorination of methyl difluoromethyl ether in the presence of a solvent to form a chlorinated reaction product of the formula $CF_2HOCH_{3-z}Cl_z$ wherein z is 1, 2 or 3. The process may also be carried out in the presence of oxygen in order to inhibit the formation of $CF_2HOCCl_3$. The resulting compound(s) is then fluorinated with HF before or after separation, to give a fluorinated reaction product including the aforementioned fluorinated dimethyl ethers.

13 Claims, No Drawings

CHLORINATION OF DIFLUOROMETHYL METHYL ETHER

BACKGROUND OF THE INVENTION

This invention relates in general to fluorinated dimethyl ethers and specifically to methyl difluoromethyl ether as a starting material for the synthesis of fluorinated dimethyl ethers. Such fluorinated dimethyl ethers, including bis(difluoromethyl)ether ($CHF_2OCHF_2$), have utility as CFC alternatives, particularly for use as refrigerants, blowing agents, etc.

Bis(difluoromethyl)ether has been prepared previously by chlorination of dimethyl ether followed by isolation and fluorination of bis(dichloromethyl)ether. The chlorination step resulted in a complex mixture of chlorinated dimethyl ethers, some of which were unstable, e.g. to distillation, from which bis(dichloromethyl)ether was separated. Moreover, chloromethyl methyl ether and bis(chloromethyl)ether are produced by this reaction, and are carcinogens.

The higher chlorinated methylethers also have been made by using either chloromethyl methylether or bis(chloromethyl)ether as starting materials. The chlorination of both these ethers, in either vapor phase or solution, is not nearly as vigorous as that of dimethyl ether, permitting easier control of the reaction. However, this approach also involves the use of the same carcinogenic ethers.

Another approach to the synthesis of methyl difluoromethyl ether is disclosed by Hine and Porter in *Methylene derivatives as intermediates in polar reaction VIII. Difluoromethyl in the Reaction of Chlorodifluoromethane with Sodium Methoxide*, published in the Journal of the American Chemical Society 79, 5493-6 (1957). This article describes a reaction mechanism wherein the desired difluoromethyl-methyl-ether is synthesized in a batch reaction in a fixed ratio with the by-product trimethyl-orthoformate, while continuously refluxing the unreacted feed. However, not only does this reaction produce large amounts of trimethylorthoformate, but also the product itself breaks down to trimethylorthoformate, resulting in less than advantageous yields of the desired difluoromethyl methyl ether.

U.S. Pat. No. 5,185,474, the disclosure of which is hereby incorporated by reference, discloses avoiding the production of such carcinogens and unstable compounds by using methyl difluoromethyl ether as a starting material. The methyl difluoromethyl ether is chlorinated to produce a reaction mixture including at least one compound of the formula $CF_2HOCH_{3-z}Cl_z$, wherein z is 1, 2, or 3. The mixture can then be fluorinated, or any one of the chlorination compounds first separated from the mixture and separately fluorinated.

However, the chlorination of an alkyl group has a high heat of reaction, which is absorbed by the reactant and products as a function of their specific heats, and then transferred through the walls of the reactor which serve as heat transfer agents. Unstable reactants and/or products, such as $CF_2HOCH_3$ and its chlorinated derivatives, have limited thermal stability and can decompose to some extent in such a system because of the temperature gradients and hot spots present in the reaction mixture.

Accordingly, it is an object of the present invention to provide an improved process for the chlorination of difluoromethylmethylether by removing the heat of reaction.

SUMMARY OF THE INVENTION

The problems of the prior art have been overcome by the present invention, which provides a process for the chlorination of difluoromethyl methyl ether either in batch mode or continuously. More specifically, the process of the present invention includes means for removing the heat of reaction and preventing exposure of thermally unstable reactants and products to excessive heat.

In addition, an unstable complex mixture of chlorinated ethers, some of which are carcinogens, in accordance with the prior art, is avoided in the present invention by employing methyl difluoromethyl ether as a starting material. The methyl difluoromethyl ether is chlorinated to give a chlorinated reaction mixture including at least one compound of the formula $CF_2HOCH_{3-z}Cl_z$, wherein z is 1, 2 or 3, which compound can be readily separated from the chlorinated reaction mixture. The chlorination of methyldifluoromethyl ether would generally form only three derivatives, i.e., $z=1$, $z=2$ and $z=3$. The dichloromethyl difluoromethyl ether ($z=2$) can be readily separated from the chlorinated reaction mixture and is then fluorinated, with or without such separation, to form the bis(difluoromethyl)ether. The production of $CF_2HOCCl_3$ ($z=3$) can be inhibited, and any produced also may be separated from the chlorination reaction product and fluorinated. Alternatively, the chlorination reaction product itself may be fluorinated (without prior separation) as follows:

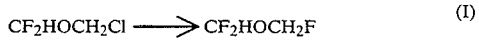

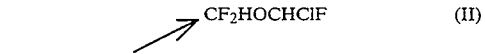

All of the above would find utility as refrigerants, especially (I) monofluoromethyl difluoromethyl ether and (II) bis(difluoromethyl) ether, which are considered to be substitutes for R-11 and R-114 refrigerants, respectively.

DETAILED DESCRIPTION OF THE INVENTION

The methyl difluoromethyl ether which is regarded as the starting material for the process of the present invention is a known compound which may be prepared in the manner reported by Hine and Porter in their aforementioned article published in the *Journal of the American Chemical Society*. Specifically, difluoromethyl methyl ether is produced by reaction of sodium methoxide (NaOMe) with chlorodifluoromethane ($CF_2HCl$), which reaction may be represented as follows:

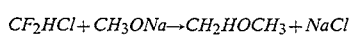

Briefly, the method involves forming an alcohol solution of sodium methoxide and bubbling the chlorodifluoromethane slowly into the reaction mixture to obtain the methyldifluoromethyl ether as a residue in the reaction mixture. Some product is entrained with unreacted $CF_2HCl$ and can be separated from it in a distillation operation.

The starting ether, $CHF_2OCH_3$, also might be prepared by first reacting NaOH with $CH_3OH$, in effect making $CH_3ONa$, and then reacting it with $CF_2HCl$. However, water is also formed in the $NaOH/CH_3OH$ reaction. The effect water has on the subsequent reaction to form $CHF_2OCH_3$ is to reduce the yield of $CHF_2CH_3$.

The chlorination and fluorination steps of this invention can be represented as follows:

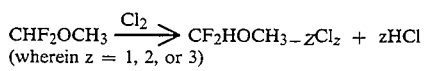
(wherein z = 1, 2, or 3)

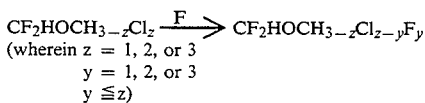
(wherein z = 1, 2, or 3
y = 1, 2, or 3
y ≦ z)

Where desired, the formation of $CF_2HOCH_{3-z}C_z$ wherein z=3 in the above reaction scheme can be inhibited or even eliminated upon the addition of an oxygen source, preferably air, to the reaction medium. Rather than inhibiting the three chlorination products equally, the addition of oxygen preferentially inhibits the formation of $CF_2HOCCl_3$. Although the inventors of the present invention are not to be limited by any mechanism theory, it is believed that the inhibition is caused as a result of oxygen forming a complex with the activated chlorine molecule, with the kinetics of the reaction being such that the trichloro derivative is preferentially inhibited. Any oxygen source not deleterious to the production of the desired compounds could be used, including oxygen-containing compounds which liberate oxygen in situ.

The oxygen should be present in an amount effective for the desired inhibition. In the case of air, preferably the air is added in an amount from about 1.5 to about 12% of the total gas flow. Those skilled in the art will recognize that where pure oxygen is used, the amounts will be about 1/5 that of air. Preferably the oxygen source is added to the reaction medium for as long as the chlorine gas is flowing.

In accordance with the present invention, $CHF_2OCH_3$ may be suitably chlorinated by combining it with chlorine gas and feeding the combination into a reactor containing a solvent for the mixture. The $CHF_2OCH_3$ can be added to the solvent as either a vapor or a liquid. If added in liquid form, a reaction temperature below its boiling point is preferable, such as a reaction temperature of about $-15°$ C. to about $-20°$ C., so as to retain most of the ether in solution and thereby avoid a heavy reflux from the cold condenser.

The reaction medium can be irradiated with a source of light, such as visible light. Alternatively, one may use other light sources such as ultraviolet light or heat, a catalyst or a free radical initiator to aid in the reaction. The chlorination products of $CHF_2OCH_3$ can be readily separated prior to fluorination or the reaction mixture can be fluorinated without separation to give an admixture of $CF_2HOCCl_2F$, $CF_2HOCF_2Cl$, $CF_2HOCH_2F$, $CF_2HOCFHCl$, $CF_2HOCF_2H$. All separations may be effected by fractional distillation.

The solvent acts as the principal heat sink for the heat generated by the reaction. The temperature can be controlled more uniformly throughout the reaction solution and kept at a moderate level. Under such conditions, thermal decomposition of the reactants and products can be kept at a minimum. The addition of air to the gas flow reduces the formation of the trichloro derivative when necessary.

Suitable solvents include aromatics and halogenated aromatics such as benzene, chlorobenzene, 1,2-dichlorobenzene and 1,2,4-trichlorobenzene; nitrobenzene; water; aqueous $FeCl_3$ (2%); aqueous hydrochloric acid (37%); methylene chloride; chloroform; carbon tetrachloride; tetrachloroethane; pentachloroethane; heptachloropropane; and octachlorobutane. In general, any highly chlorinated alkane with melting points below about 100° C. can be used. At higher temperatures, difluoromethyl methyl ether and its chlorinated derivatives undergo thermal degradation. Other suitable halogenated solvents include liquid fluorocarbons, including halocarbon oils (polymers of $CF_2=CFCl$), perfluoroalkanes and perfluoroalicyclics such as perfluorocyclohexane and perfluorodecalin; highly fluorinated ethers and perfluorinated polyethers; and perfluorinated amines of suitable liquid range. Other suitable solvents include acids such as glacial acetic acid, aqueous acetic acid solutions and hydrochloric acid; and dimethylformamide. The reactants should be fed into the solvent at a suitable rate, depending in part on the volume of solvent present, so as to provide an acceptable reaction rate.

In the preferred fluorination procedure, the chlorinated reaction product is reacted with anhydrous hydrogen fluoride (HF), which reaction may be represented as follows:

$2CF_wHOCCl_3+3HF\rightarrow CF_2HOCFCl_2+CF_2Cl+3HCl$

Utilizing the above reaction with hydrogen fluoride has resulted in a yield as high as 78% $CF_2HOCF_2Cl$ with a small amount of $CF_2HOCFCl_2$. This was an unexpected result since HF by itself does not normally replace a halogen such as chlorine, except perhaps at very high temperatures, but instead fluorinates by continuous regeneration of a fluorinating agent such as $SbCl_{5-y}F_y$, 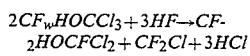 such as $SbF_3$, or $SbF_3CL_2$. Apparently, the difluoromethoxy group activates the chlorine on the alpha-carbon atom, allowing it to react readily with HF.

Alternatively, the HF may be diluted with any solvent with which it is miscible and unreactive, preferably an organic solvent, most preferably a dipolar aprotic solvent such as methyl pyrrolidone, in order to reduce fragmentation of the fluorinated material, resulting in higher yields of desired product with less by-product generation. Other sources of fluorine for the fluorination step include metal fluorides that can form salts of the $HF_2^\ominus$ anion, such as $NaHF_2$, $NaHF_2$, $LiHF_2$, $NH_4HF_2$, etc.; pyridine, amines, and other electron pair donor bases which can form complexes of the general formula $BH+(HF)_xF^-$ (wherein B is a donor base); and alkali metal fluorine salts such as NaF and KF in suitable solvents. Examples of donor bases include carbamic acids and their esters, amides, trialkyl phosphines, etc.

The resultant fluorinated products may be separated by distillation or by the process as taught in U.S. Pat. No. 4,025,567 or U.S. Pat. No. 3,887,439 which are incorporated herein by reference in their entirety.

The present invention will now be further illustrated by the following examples.

EXAMPLES

The chlorination apparatus consisted of a jacketed resin flask of suitable size, usually 500 ml. volume, to which was attached a jacketed condenser connected to a Dewar condenser. The individual gases were passed through flowmeters and then combined and fed into the reaction flask through a sparge tube which was immersed in the solvent. The volume of solvent was about ⅔ the volume of the flask. A thermocouple was inserted through another opening in the flask head to monitor the temperature of the reaction medium. Coolant from a refrigerated bath was circulated through the jackets of the flask and vertical condenser.

Acetone/dry ice was placed in the Dewar condenser. Irradiation was provided by a 150 watt incandescent spotlight. At the completion of the reaction, the solvent was removed and analyzed by GC for the chlorinated products. The results are shown in Table I.

The Table illustrates the effects of changes in variables such as mole ratio of $Cl_2/CF_2HOCH_3$ and addition of air to the gas mixture on the total conversion $CF_2HOCH_3$ to chlorinated ethers and the distribution of those ethers in the product mixture. Comparison of the runs which included the addition of air with runs that did not shows the inhibiting effect of the air on the formation of $CF_2HOCCl_3$. The use of halocarbon oil as the solvent did not require the addition of air to inhibit $CF_2HOCCl_3$ formation.

What is claimed is:

1. A process for the preparation of fluorinated dimethyl ethers of the formula $CF_2HOCCl_xF_yH_{3-(x+y)}$, wherein x is 0, 1 or 2 and y is 1, 2 or 3 and wherein the total of x+y 1, 2, or 3, said process comprising:

chlorinating $CHF_2OCH_3$ by reacting said $CHF_2OCH_3$ with chlorine in the presence of a solvent in an amount effective to dissolve the mixture of said $CHF_2OCH_3$ and chlorine to form a chlorinated admixture containing at least one compound of the formula $CF_2HOCH_{3-z}Cl_z$, wherein z is 1, 2 or 3;

fluorinating said at least one compound of the formula $CF_2HOCH_{3-z}Cl_z$ with a fluorine source selected from the group consisting of hydrogen fluoride, anhydrous hydrogen fluoride, metal salts of $HF_2^\ominus$, NaF, KF, pyridine, amine, and other electron pair donor bases which form complexes of the general formula $BH^+(HF)_xf^-$ (wherein B is a donor base), in the absence of a catalyst to obtain a fluorinated admixture containing at least one compound of formula $CF_2HOCH_{3-z}F_yCl_{z-y}$.

2. A process in accordance with claim 1 wherein said chlorination step is carried out in the presence of oxygen in order to inhibit the formation of $CF_2HOCCl_3$.

3. A process in accordance with claim 1 wherein the hydrogen fluoride is selected from the group consisting of anhydrous hydrogen fluoride and hydrogen fluoride in an organic solvent.

4. A process in accordance with claim 1 wherein said at least one compound of the formula $CF_2HOCH_{3-z}Cl_z$ is $CF_2HOCHCl_2$ and said fluorinated reaction product includes $CF_2HOCF_2H$ and $CF_2HOCHFCl$.

TABLE 1

Chlorination of Difluoromethylmethylether

| Run No. | Solvent | Flow Rates $Cl_2$ mls/min. | Flow Rates E-152a[1] mls/min. | Flow Rates Air mls/min. | Moles $Cl_2$ | Moles E-152a[1] | Mole Ratio $Cl_2$/E-152a[1] | Air in Total Gas Flow % | Temp °C. | Total Conversion % | Product Distribution Mono % | Product Distribution Di % | Product Distribution Tri % |
|---|---|---|---|---|---|---|---|---|---|---|---|---|---|
| 1 | 1,2-Dichlorobenzene | 97.0 | 23.4 | — | 0.860 | 0.208 | 4.15 | — | 22 | 95.8 | 36.9 | 47.1 | 11.8 |
| 2 | 1,2-Dichlorobenzene | 64.1 | 27.4 | — | 0.409 | 0.175 | 2.34 | — | 31 | 87.7 | 43.9 | 37.2 | 6.6 |
| 3 | 1,2-Dichlorobenzene | 92.4 | 24.4 | — | 0.703 | 0.186 | 3.10 | — | 15 | 91.7 | 23.0 | 43.8 | 24.9 |
| 4 | 1,2-Dichlorobenzene | 90.7 | 18.7 | 7 | 0.790 | 0.153 | 5.17 | 6.4 | 20 | 90.8 | 71.0 | 19.8 | 0 |
| 5 | 1,2-Dichlorobenzene | 93.3 | 20.4 | 3 | 0.804 | 0.153 | 5.25 | 2.6 | 20 | 96.3 | 61.6 | 32.2 | 2.5 |
| 6 | 1,2,4-Trichlorobenzene | 122.2 | 22.8 | — | 0.899 | 0.153 | 5.81 | — | 15–30 | 97.3 | 0 | 5.3 | 92 |
| 7 | 1,2,4-Trichlorobenzene | 73.4 | 26.1 | 7 | 0.508 | 0.175 | 2.91 | 7.0 | 15–30 | 85.6 | 8.4 | 38.9 | 38.3 |
| 8 | 1,2,4-Trichlorobenzene | 48.5 | 38.5 | 7 | 0.353 | 0.280 | 1.26 | 8.0 | 15–30 | 87.4 | 64.6 | 22.2 | 0.6 |
| 9 | 1,2,4-Trichlorobenzene | 57.2 | 36.6 | 9 | 0.480 | 0.307 | 1.56 | 9.6 | 15–30 | 92.7 | 52.0 | 37.0 | 3.7 |
| 10 | 1,2,4-Trichlorobenzene | 51.2 | 42.1 | 11 | 0.423 | 0.338 | 1.25 | 11.8 | 15–30 | 87.5 | 72.4 | 15.1 | 0 |
| 11 | Halocarbon oil 1.8 | 88.2 | 43.1 | — | 1.044 | 0.51 | 2.05 | — | 0–3 | 97.6 | 74.1 | 23.5 | 0 |
| 12 | Halocarbon oil 1.8 | 63.2 | 46.8 | — | 0.550 | 0.407 | 1.35 | — | 7–18 | 97.5 | 69.5 | 28.0 | 0 |
| 13 | Halocarbon oil 1.8 | 85.3 | 27.3 | — | 0.790 | 0.252 | 3.13 | — | 8–12 | 97.4 | 4.0 | 44.8 | 48.6 |
| 14 | Water | 81.7 | 54.8 | — | 1.284 | 0.715 | 1.80 | — | 4–7 | 64.4 | 24.3 | 31.9 | 8.2 |
| 15 | Water + 2% $FeCl_3$ | 166.9 | 41.1 | — | 2.906 | 0.715 | 4.06 | — | 5–7 | 84.2 | 0 | 2.7 | 81.5 |
| 16 | Aq.HCl (37%) | 45.9 | 54.9 | — | 0.860 | 0.881 | 0.98 | — | −4 | 23.2 | 12.8 | 9.3 | 1.1 |
| 17 | Chlorobenzene | 84.4 | 29.5 | — | 0.550 | 0.175 | 3.14 | — | 22 | 40.3 | 40.3 | 0 | 0 |

Note [1] E-152a is difluoromethylmethylether, $CF_2HOCH_3$

5. A process in accordance with claim 1 wherein said at least one compound of the formula $CF_2HOCH_{3-z}Cl_z$ is $CF_2HOCHCl_2$ and said at least one compound of the formula $CF_2HOCCl_xF_yH_{3-(x+y)}$ is $CF_2HOCF_2H$, and further comprising separating and recovering said $CF_2HOCF_2H$ from said fluorinated admixture.

6. A process in accordance with claim 1 further comprising reacting $CHF_2Cl$ with an alkali metal methoxide in solvent solution to form said $CHF_2OCH_3$.

7. A process in accordance with claim 2, wherein air is the source of said oxygen.

8. The process in accordance with claim 1, wherein said solvent is selected from the group consisting of 1,2-dichlorobenzene, 1,2,4-trichlorobenzene and halocarbon oil.

9. The process in accordance with claim 1 wherein the process is conducted in a continuous mode.

10. The process in accordance with claim 1, wherein said fluorine source is selected from the group consisting of NaF in a suitable solvent and KF in a suitable solvent.

11. A process for chlorinating $CHF_2OCH_3$, comprising reacting said $CHF_2OCH_3$ with chlorine in the presence of a solvent to form a chlorinated admixture containing at least one compound of the formula $CF_2HOCH_{3-z}Cl_z$, wherein z is 1, 2 or 3.

12. The process of claim 10, further comprising reacting said $CHF_2OCH_3$ in the presence of an oxygen source.

13. The process of claim 11, wherein said oxygen source is air.

* * * * *